US006774371B2

(12) United States Patent
Garrard et al.

(10) Patent No.: US 6,774,371 B2
(45) Date of Patent: Aug. 10, 2004

(54) METHOD AND APPARATUS FOR A MULTI-PLANAR IMAGING SYSTEM

(75) Inventors: Jody Garrard, Elk Grove, CA (US); Jeffrey Hallett, Livermore, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 159 days.

(21) Appl. No.: 09/989,228

(22) Filed: Nov. 20, 2001

(65) Prior Publication Data

US 2003/0094577 A1 May 22, 2003

(51) Int. Cl.[7] ............................................... G01T 1/161
(52) U.S. Cl. ........................... 250/363.08; 250/363.02
(58) Field of Search ..................... 250/363.08, 363.02, 250/363.05, 363.01, 361 R, 336.1, 363.04

(56) References Cited

U.S. PATENT DOCUMENTS 6,150,662 A   11/2000  Hug et al.
RE37,474 E  * 12/2001  Hug et al. ............. 250/363.08

* cited by examiner

Primary Examiner—David Porta
Assistant Examiner—Christine Sung

(57) ABSTRACT

The invention comprises a system and method for multi-planar imaging using a plurality of detectors coupled to an ECDAS. Each of the plurality of detectors is independently positionable and configurable to acquire image data of one or more patients, and is controlled by the ECDAS. The ECDAS operates in at least two modes. A first mode, the ECDAS configures the plurality of detectors to collect image data for a single procedure of a single patient. A second mode, ECDAS configures the plurality of detectors to collect image data of a plurality of patients simultaneously.

20 Claims, 6 Drawing Sheets

METHOD AND APPARATUS FOR A MULTI-PLANAR IMAGING SYSTEM

TECHNICAL FIELD

The invention relates to medical imaging systems for viewing anatomical structures and functions of a patient and, more particularly, to a multi-planar imaging system that increases the throughput of a multi-detector imaging system.

BACKGROUND OF THE INVENTION

Nuclear imaging systems generally utilize a detector positioned about a patient for the purpose of collecting data regarding anatomical structures and bodily functions of the patient. Each detector is capable of collecting data for a single patient at any given moment. As a result, the number of patients that may utilize the nuclear imaging system within a given amount of time is limited.

Nuclear imaging systems have been developed to reduce the amount of time required to perform a given procedure. One such development has been a dual-imaging system, which utilizes two detectors that operate simultaneously. By utilizing two detectors to collect the information that was previously collected by a single detector, the amount of time a procedure requires is reduced.

Some procedures, such as renal, GI bleed, hepatobiliary, gallbladder, thyroid, and the like, however, only use a single detector. When a dual-imaging system is utilized to perform one of these procedures, one of the detectors is unused. As a result, a valuable resource, i.e., a detector, is idle for the entire length of time that the procedure requires.

Therefore, there is a need for a method and a system to provide nuclear imaging in an efficient manner that reduces the length of time that a resource remains idle.

SUMMARY OF THE INVENTION

The invention comprises a system and method for multi-planar imaging using a plurality of detectors coupled to an electronic controller and data acquisition system. The electronic controller and data acquisition system is capable of configuring the plurality of detectors in at least two modes. A first mode configures the plurality of detectors to collect image data for a single procedure of a single patient. A second mode configures the plurality of detectors to collect image data of a plurality of patients simultaneously.

BRIEF DESCRIPTION OF THE DRAWINGS

For a more complete understanding of the present invention, and the advantages thereof, reference is now made to the following description taken in conjunction with the accompanying drawings, in which.

DETAILED DESCRIPTION

In the following discussion, numerous specific details are set forth to provide a thorough understanding of the present invention. However, it will be obvious to those skilled in the art that the present invention may be practiced without such specific details. In other instances, well-known elements have been illustrated in schematic or block diagram form in order not to obscure the present invention in unnecessary detail. Additionally, for the most part, details concerning imaging and the like have been omitted inasmuch as such details are not considered necessary to obtain a complete understanding of the present invention, and are considered to be within the skills of persons of ordinary skill in the relevant art.

The principles of the present invention and their advantages are best understood by referring to the illustrated embodiments in FIGS. 1–8.

Figure 1:
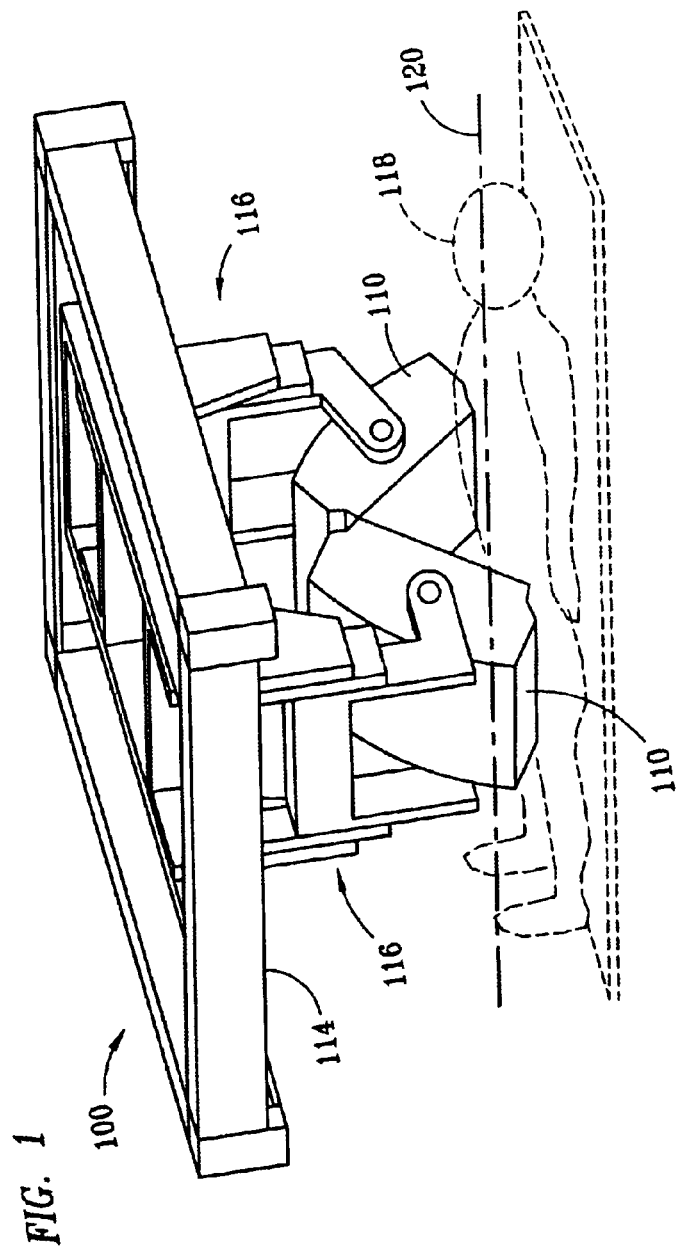
FIG. 1 illustrates a multi-detector/single planar imaging system incorporating features of the present invention.

Referring to FIG. 1 of the drawings, the reference numeral 100 generally designates a dual-detector imaging system, such as one disclosed in U.S. Pat. No. 6,150,662, issued to Hug et al. (hereinafter "Hug"), and filed on Apr. 30, 1998, which is incorporated herein for all purposes. Generally, the dual-detector imaging system 100 comprises detectors 110 suspended from a gantry 114 via support arms 116, the detectors 110 being independently configurable in a plurality of positions and angles relative to a longitudinal axis 120 of an object 118, such as a patient placed on a hospital gurney. The detectors 110 may be suspended by any appropriate method, such as those described by Hug.

The dual-detector imaging system 100 may be utilized as either a single-detector imaging system or a dual-detector imaging system. The detectors 110 are configurable to operate in tandem for a single procedure that generally requires dual detectors, such as an ECT, Total Body, and the like. One of the detectors 110, however, is not used for procedures requiring only a single detector, such as renal, GI bleed, hepatobiliary, gallbladder, thyroid, and the like.

Figure 2:
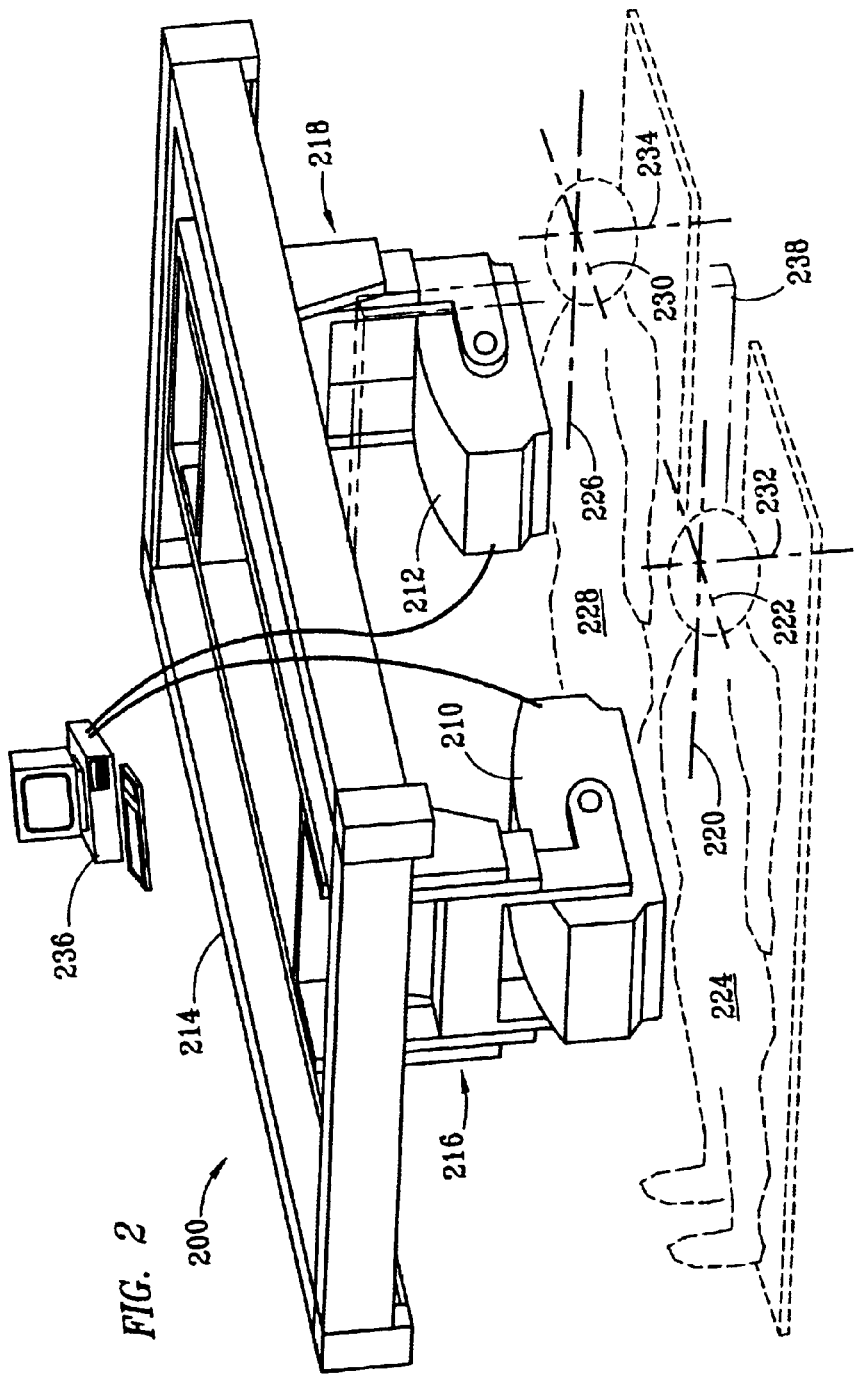
FIG. 2 illustrates a dual-detector/dual-planar imaging system incorporating features of the present invention.

FIG. 2 illustrates a dual-planar imaging system 200 embodying features of the present invention. Preferably, the dual-planar imaging system 200 provides all operational features of the dual-detector imaging system 100 (FIG. 1) in addition to the features discussed within this disclosure, such as dual-planar imaging. It should be noted, however, that the dual-planar imaging system 200 is presented for illustrative purposes only, and, in particular, multi-planar imaging systems with fewer or more detectors, such as three or more, are included within the scope of the present invention.

The dual-planar imaging system 200 preferably comprises a first detector 210 and a second detector 212 suspended from a gantry 214 via a first support arm 216 and a second support arm 218, respectively. The gantry 214 is preferably mounted on posts, attached to the ceiling, or the like, to raise the gantry 214 to a height sufficient to allow users to comfortably walk upright underneath the gantry 214.

Preferably, the gantry 214 allows the first detector 210 to translate substantially parallel to a first longitudinal axis 220 of a first object 224. Additionally, it is preferred that the gantry allows the first support arm 216 to translate substantially parallel to a first horizontal axis 222, which is substantially perpendicular to the first longitudinal axis, in order to allow the first detector 210 to be horizontally adjusted relative to the first longitudinal axis 220, including over and/or under, the first object.

Similarly, the gantry 214 allows the second detector 212 to translate substantially parallel to a second longitudinal axis 226 of a second object 228, and allow the second support arm 218 to translate substantially parallel to a second horizontal axis 230, which is substantially perpendicular to the second longitudinal axis 226, in order to allow the second detector to be horizontally adjusted relative to the second longitudinal axis 226, including over and/or under the second object 228.

Furthermore, the support arms 216 and 218 are preferably adjustable via a telescopic arm, rollers, guides, rails, and/or the like, to allow for the vertical adjustment, i.e., translation substantially parallel to a first vertical axis 232 and a second vertical axis 234, respectively. Optionally, the first detector 210 and the second detector 212 are rotatably connected to the first support arm 216 and the second support arm 218, respectively, such that the detectors may be rotatably positioned about one or more axis, such as the corresponding longitudinal axis, the horizontal axis, and/or the vertical axis.

An electronic controller and data acquisition system (ECDAS) 236 is coupled to the first detector 210 and the second detector 212. The ECDAS 236 is configured to control the movement and operation of the first detector 210 and the second detector 212. The ECDAS 236 preferably comprises a computer system configured to accept commands and provide system information, preferably via a graphical user interface (GUI), such as that discussed below with reference to FIGS. 5–6, and coupled to a keyboard, mouse, and/or other means of inputting data acquisition parameters, such as a touch screen, touch panel, and/or the like.

The ECDAS 236 communicates data acquisition parameters selected by a user (not shown) to the first detector 210 and/or the second detector 212, which use the data acquisition parameters to acquire imaging data regarding the first object 224 and/or the second object 228. The data acquisition parameters, such as matrix, detector masks, orientation, and the like, configure the computer to sort the acquisition data into the proper format for static, dynamic, and/or gated planar studies. For example, a thyroid scan may be set to acquire a static planar acquisition using a 256×256 matrix, 25 cm detector mask, 0-degree orientation, with stop criteria at 500,000 collected events. Furthermore, the first detector 210 and the second detector 212 are configured to transfer imaging data to the ECDAS 236 for post-acquisition processing.

An optional interference screen 238 prevents interference between the first detector 210 and the second detector 212 when the detectors are positioned such that the operation of one may affect the operation of the other, commonly referred to as cross-talk, such as may occur when the detectors are positioned facing each other. Cross-talk is generally a scatter phenomenon where photons from one patient, which is being scanned by one detector, are acquired by a second detector, which is being used to scan a second patient, thereby corrupting the results. In order to prevent cross-talk from occurring, an interference screen 238, such as a lead screen, that is known to block or prevent cross-talk is positioned between the first detector 210 and the second detector 212. It should be noted that the interference screen 238 is not normally required when the first detector 210 and the second detector 212 are positioned such that the first detector 210 and the second detector 212 do not face each other, such as when the detectors are positioned above the respective objects and directed downward and/or when the detectors are positioned below the respective objects and directed upward.

Additionally, a optional privacy screen (not shown) may be positioned between the first detector 210 and the second detector 212 to provide privacy to the patients, i.e., the first object 224 and the second object 228.

In operation, the dual-planar imaging system 200 may be configured to operate as a single-imaging/single-planar imaging system, a dual-imaging/single-planar imaging system, or a dual-planar imaging system. As a single-imaging/single-planar imaging system, only a single detector is utilized, thereby under-utilizing the system resources of the dual-planar imaging system 200.

As a dual-imaging/single-planar imaging system, the first detector 210 and the second detector 212 are positioned about an object, such as illustrated in FIG. 1. The first detector 210 and the second detector 212 are configured to collect data regarding a single procedure for a single patient. In this configuration, the length of time that a single procedure requires is reduced by utilizing both detectors.

As a dual-planar imaging system, the first detector 210 and the second detector 212 are separated and positioned appropriately about a first and second patient, respectively, and are independently configurable and operable. The interference screen 238 is utilized as discussed above to prevent cross-talk, and the optional privacy screen provides confidentiality among patients. The ECDAS 236 manages the configuration and operation of the first detector 210 and the second detector 212 for simultaneous imaging of the first and second patient.

Figure 3:
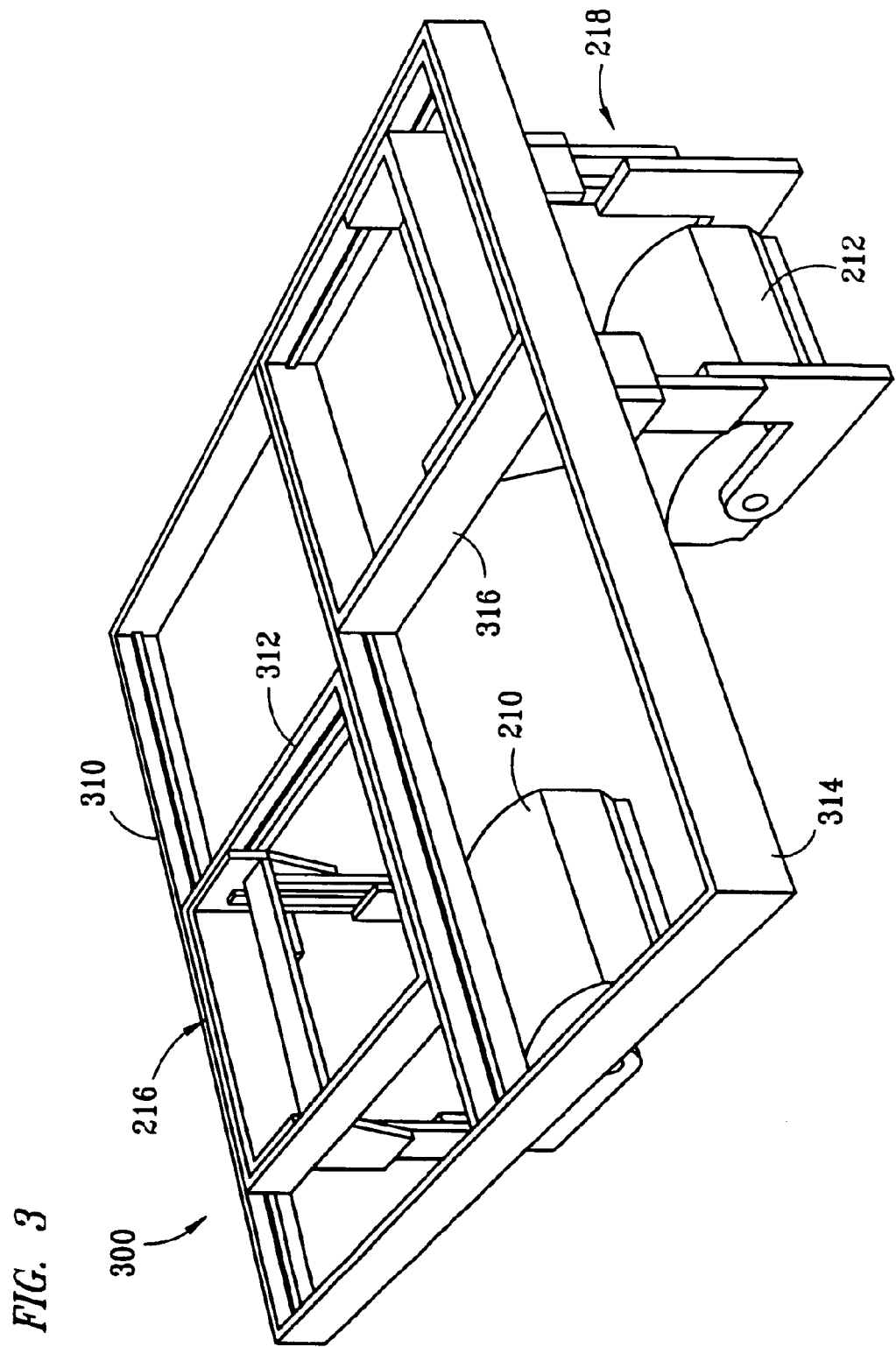
FIG. 3 illustrates a single-gantry system that provides multi-dimensional movement of detectors in a multi-detector/multi-planar imaging system.

FIG. 3 schematically depicts one embodiment of a single-gantry system 300 for the dual-planar system 200 (FIG. 2) that embodies features of the present invention. The single-gantry system 300 comprises a first outer carriage 310 that provides translational movement substantially parallel to the first longitudinal axis 220 for a first inner carriage 312, which provides translation movement substantially parallel to the first horizontal axis 222 for the first support arm 216. The first inner carriage 312 is preferably mounted to the first outer carriage 310 in a manner to allow for motorized, manual, and/or power-assisted movement, such as by the use of rails, rollers, guides, hydraulics, and/or the like. Additionally, the first inner carriage 312 is preferably mounted to the first outer carriage 310 in a like manner.

A second outer carriage 314 and a second inner carriage 316 are similarly configured.

It should be noted, however, that the single-gantry system 300 is depicted to comprise a first outer carriage 310 and a second outer carriage 314 of approximately equal dimensions for illustrative purposes only. Accordingly, the first outer carriage 310 and the second outer carriage 314 may have differing dimensions, such as a first outer carriage 310 and/or a first inner carriage 312 that provides a smaller range of motion than the second outer carriage 314 and/or the second inner carriage 316, or the like.

Figure 4:
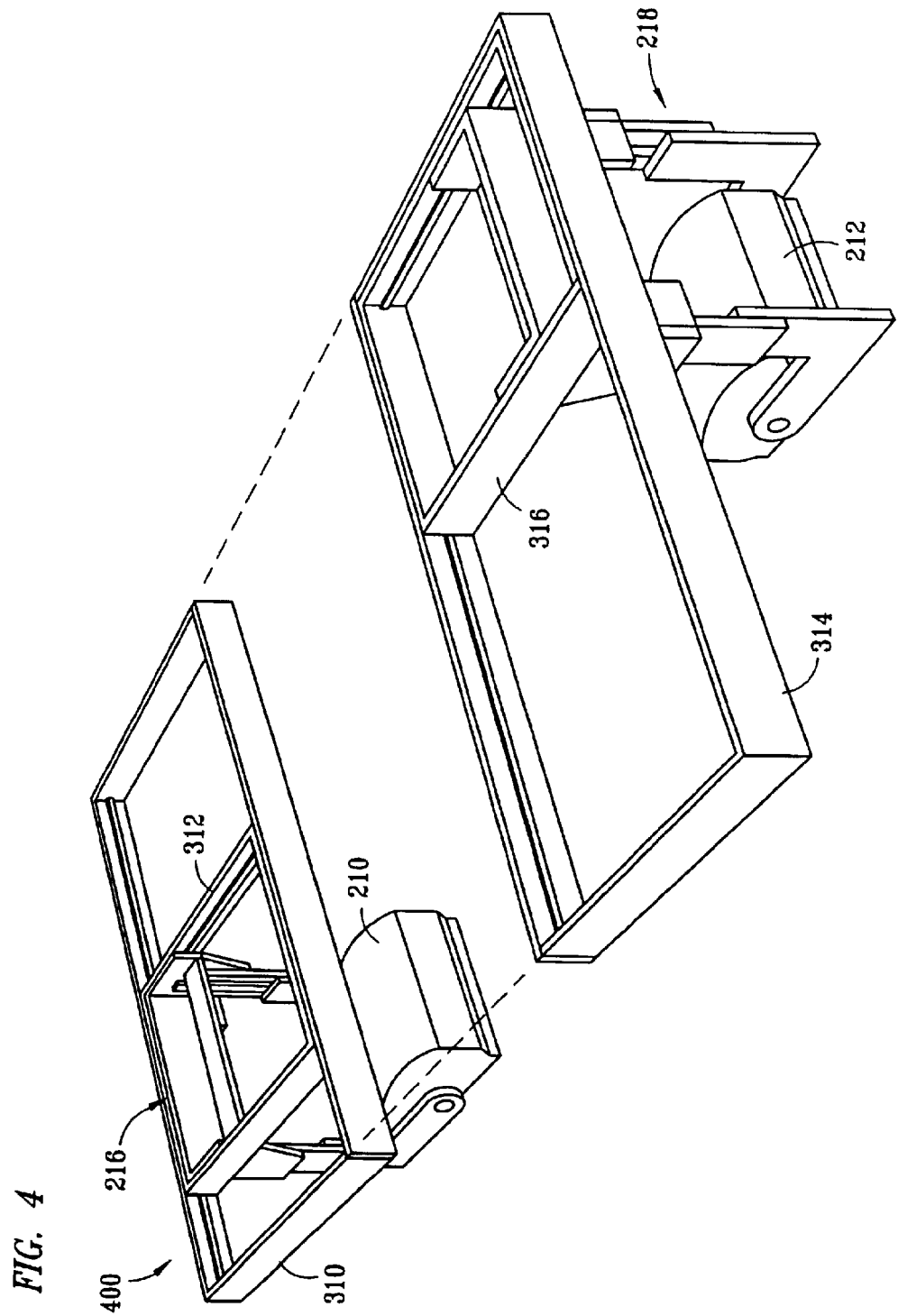
FIG. 4 illustrates a dual-gantry system that provides multi-dimensional movement of detectors in a multi-detector/multi-planar imaging system.

FIG. 4 schematically depicts one embodiment of a dual-gantry system 400 for the dual-planar system 200 (FIG. 2) in accordance with the present invention. The dual-gantry system 400 is similar to the single-gantry system 300 except that the first outer carriage 310 is separated from the second outer carriage 314. The structure of the dual-gantry system 400 is described above with reference to the single-gantry system 300, where like-numbered elements perform similar functions.

It should be noted that the orientation and translational and/or rotational movement depicted by the single-gantry system 300 (FIG. 3) and the dual-gantry system 400 (FIG. 4) are for illustrative purposes only, and should not limit the present invention to such specific embodiments. For example, the orientation of the inner and outer carriages may be rotated 90 degrees and maintain the translational capabilities along the longitudinal axis and the horizontal axis. As such, the various orientations and configurations should be considered within the scope of the present invention.

Figure 5:
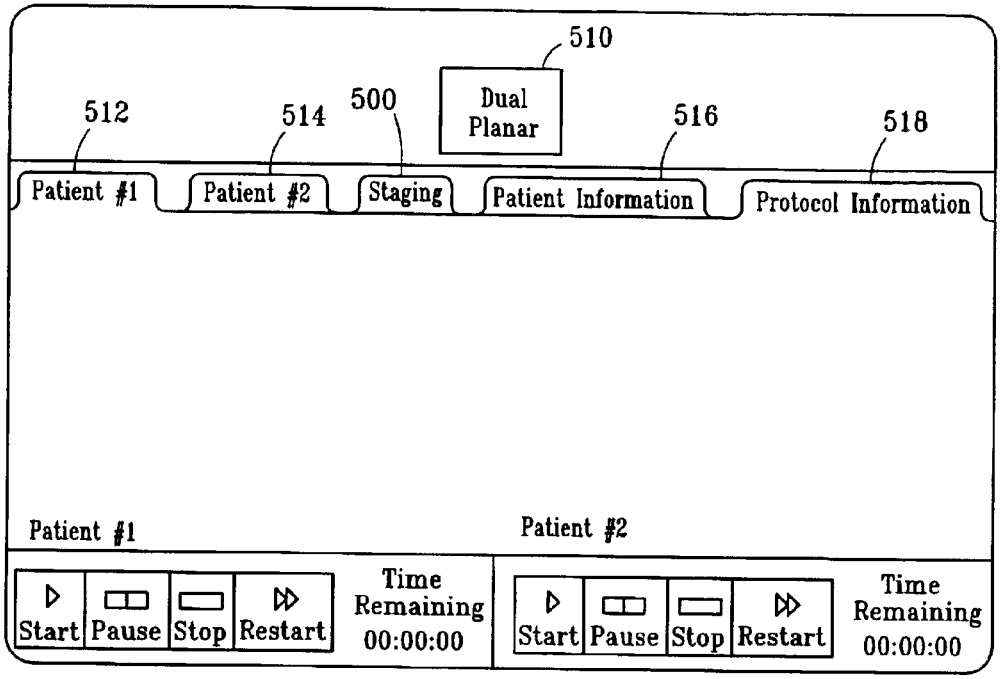
FIG. 5 illustrates a full-screen graphical-user interface (GUI) embodying features of the present invention.

FIG. 5 depicts one embodiment of a full-screen GUI that may be presented to a user by the ECDAS in accordance with the present invention. The full-screen GUI depicts information and capabilities that would be available upon selecting a dual-planar command 510. The user selects either a patient #1 control 512 or patient #2 control 514 to view and/or modify patient information 516 and/or protocol information 518, such as the type of view, type of injection, scanning parameters, and the like. The content of the patient information 516 and/or protocol information 518 is considered well known to a person of ordinary skill in the art upon a reading of the present disclosure, and, therefore, will not be discussed in greater detail. Optionally, a staging command 520 may be available to allow a user to set-up the next patient while imaging procedures are being conducted.

Due to the large amounts of information, it is preferred that the information is displayed largely in a full-screen mode, i.e., patient information is displayed for the selected patient. Patient #1 control 512 and patient #2 control 514, however, are preferably always available to allow quick and easy access during the imaging procedures.

Figure 6:
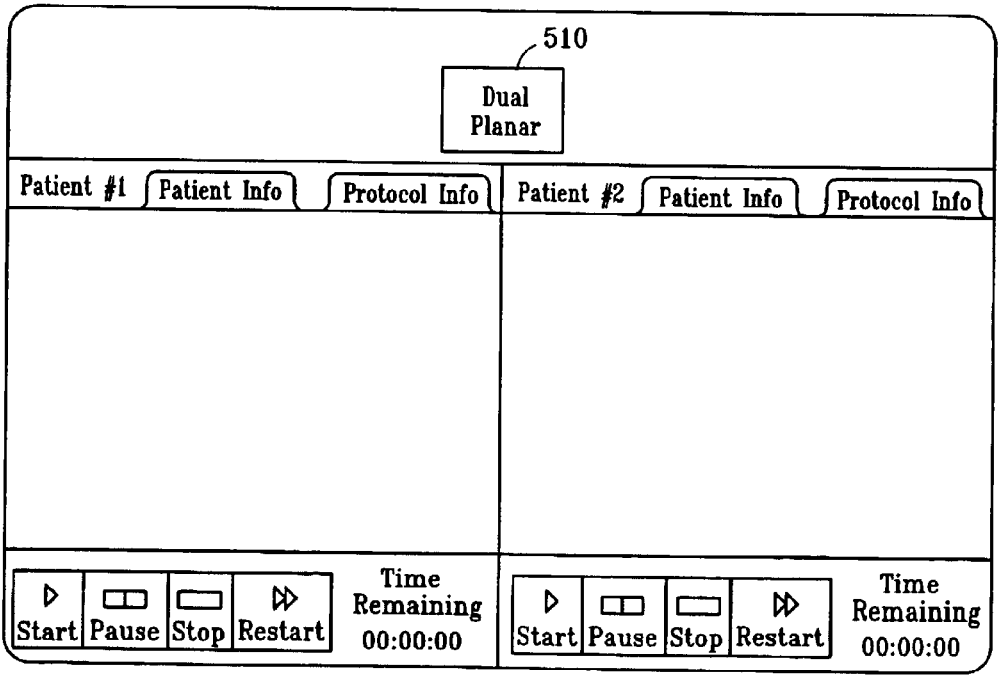
FIG. 6 illustrates a split-screen GUI embodying features of the present invention.

FIG. 6 depicts one embodiment of a split-screen GUI that may be presented to a user by the ECDAS in accordance with the present invention. The split-screen GUI provides equivalent functionality as the full-screen GUI except that all or a sub-set of the patient data is displayed simultaneously. Preferably, the user is given an option, such as the full-screen command, or the like, that allows the user to switch between the split-screen GUI and the full-screen GUI.

Figure 7:
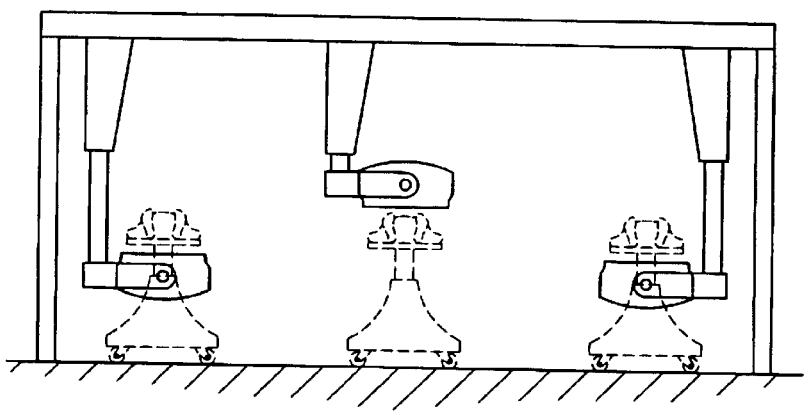
FIG. 7 illustrates a tri-detector/tri-planar imaging system incorporating features of the present invention.

FIG. 7 illustrates an alternative embodiment of a multi-planar imaging system comprising three detectors in accordance with the present invention. It should be noted that the illustration and discussion in the present disclosure depicting the multi-planar system as a dual-planar imaging system 200 and a tri-planar imaging system 700 is for illustrative purposes only, and should not be interpreted as limiting the present invention in any manner. The configuration and operation of a multi-planar system with any number of detectors is considered well known to one of ordinary skill in the art upon a reading of the present disclosure.

Figure 8:
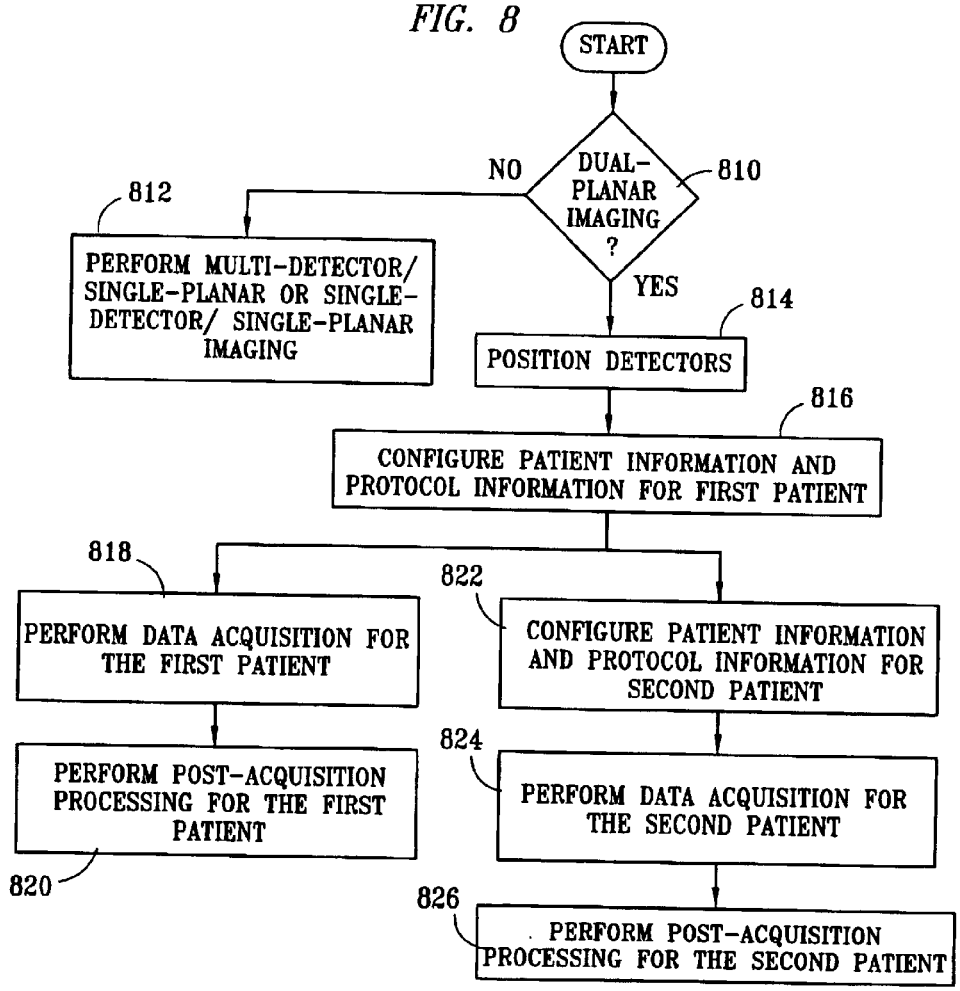
FIG. 8 is a flow chart illustrating the steps that may be performed for dual-planar imaging.

FIG. 8 is a flow chart depicting steps that may be performed in a dual-planar imaging system, such as that depicted in FIG. 2, in accordance with one embodiment of the present invention that allows for dual-planar imaging. Processing begins in step 810, wherein a determination is made of whether dual-planar imaging is selected. If, in step 810, a determination is made that dual-planar imaging has not been selected, then processing proceeds to step 812, wherein the standard multi-detector/single-planar imaging or single-detector/single-planar imaging is performed. The process of performing multi-detector/single-planar imaging and single-detector/single-planar imaging is considered well known to a person of ordinary skill in the art upon a reading of the present disclosure, and, therefore, will not be discussed in greater detail.

If, in step 810, a determination is made that dual-planar imaging has been selected, then processing proceeds to step 814, wherein the detectors are positioned. Preferably, the ECDAS warns the user to remove all objects in the path of the detectors, and requires acknowledgement that all objects have been removed from the path of the detectors. Upon receiving an acknowledgement, the first detector and the second detector are released and positioned.

Optionally, the ECDAS may, upon acknowledgement that all objects in the path of the detectors have been removed, automatically position the first detector and the second detector to a starting position, preferably to opposing locations furthest away from each other in order to provide ample room in which to position the first and second patient.

In step 816, the patient information and protocol information, i.e., the acquisition data, of a first patient is entered. Preferably, the user enters specific information and/or selects standard acquisition parameters. The acquisition data specifies, among other things, the type of view, such as anterior, posterior, or the like, type and amount of injection, scanning parameters, such as start/stop times, counts, saturation, and the like, patient orientation, and/or the like. Upon completion of setting-up the first patient, the processing proceeds along parallel paths to steps 818 and 822.

First, the processing may proceed to step 818, wherein the first detector performs data acquisition for the first patient. In step 820, post-data acquisition processing, such as constructing an image, and providing the image and relevant information to the user, for the first patient is performed.

Second, the processing may proceed from step 816 to step 822, wherein the patient information and protocol information for a second patient is entered. In step 824, the second detector performs data acquisition the second patient, and, in step 826, post-data acquisition processing for the second patient is performed.

It is understood that the present invention can take many forms and embodiments. Accordingly, several variations may be made in the foregoing without departing from the spirit or the scope of the invention. For example, splitting the detector carriage to move the detectors to opposite corners of the room, not simply to opposite sides of the room.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Accordingly, it is appropriate that the appended claims be construed broadly and in a manner consistent with the scope of the invention.

What is claimed is:

1. A medical imaging apparatus, comprising:
  a plurality of detectors for acquiring image data of one or more patients simultaneously;
  a gantry for positioning the plurality of detector means about one or more patients;
  an electronic controller and data acquisition system for configuring and controlling the operation of the plurality of detectors in a plurality of modes, a first mode being that the plurality of detectors acquires image data of a first patient, and a second mode being that the plurality of detectors acquires image data of a plurality of patients simultaneously.

2. The medical imaging apparatus of claim 1, wherein the gantry suspends the first detector and the second detector from above the patient.

3. The medical imaging apparatus of claim 1, wherein the gantry suspends the first detector from a first support arm and the gantry suspends the second detector from a second support arm.

4. The medical imaging apparatus of claim 1, wherein the gantry suspends the first detector from a first support arm and the gantry suspends the second detector from a second support arm; wherein the gantry is configured to position the first support arm along a first longitudinal axis and a first horizontal axis, the first horizontal axis being perpendicular to the first longitudinal axis; the gantry is able to position the second support arm along a second longitudinal axis and a second horizontal axis, the second horizontal axis being perpendicular to the second longitudinal axis; the first support arm is configured to position the first detector along a first vertical axis being perpendicular to the plane formed by the first longitudinal axis and the first horizontal axis; and the second support arm is configured to position the second detector along a second vertical axis being perpendicular to the plane formed by the second longitudinal axis and the second horizontal axis.

5. The medical imaging apparatus of claim 1, wherein the electronic controller and data acquisition system comprise a graphical user interface.

6. The medical imaging apparatus of claim 1, wherein the electronic controller and data acquisition system comprise graphical user interface capable of in at least one of a full-screen mode displaying information regarding one of the first patient and the second patient and a split-screen mode simultaneously displaying information regarding the first patient and the second patient.

7. A medical imaging apparatus, comprising:
a first detector for acquiring image data of a first patient;
a second detector for acquiring image data of at least one of the first patient and a second patient;
a gantry coupled to the first detector and the second detector for positioning the first detector and the second detector at a plurality of positions about one or more axes for acquisition of image data, wherein the gantry is able to position the first detector and the second detector such that the first detector may acquire image data of the first patient simultaneously as the second detector acquires image data of the second patient, and wherein the gantry is able to position the first detector and the second detector such that the first detector and the second detector may acquire image data of the first patient; and
an electronic controller and data acquisition system for configuring and controlling the operation of the first detector and the second detector in a plurality of modes, a first mode being that at least one of the first detector and the second detector acquires image data of a first patient, and a second mode being that the first detector and the second detector acquire image data of a plurality of patients simultaneously.

8. The medical imaging apparatus of claim 7, wherein the gantry suspends the first detector and the second detector from above the patient.

9. The medical imaging apparatus of claim 7, wherein the gantry suspends the first detector from a first support arm and the gantry suspends the second detector from a second support arm.

10. The medical imaging apparatus of claim 7, wherein the electronic controller and data acquisition means comprise a graphical user interface.

11. The medical imaging apparatus of claim 7, wherein the electronic controller and data acquisition means comprise graphical user interface capable of in at least one of a full-screen mode displaying information regarding one of the first patient and the second patient and a split-screen mode simultaneously displaying information regarding the first patient and the second patient.

12. A medical imaging apparatus, comprising:
a first detector means for acquiring image data of a first-object;
a second detector means for one of: acquiring image data of the first object in coordination with the first detector and acquiring image data of a second object independent of the first detector, the second object being separate and independent from the first object;
a gantry means for positioning the first detector and the second detector at a plurality of positions about one or more axes for acquisition of image data;
an electronic controller and data acquisition means coupled to the first detector and the second detector for configuring and collecting image data, wherein the electronic controller and data acquisition means is configured for controlling the first detector collecting image data for a first object and for controlling the second detector collecting image data for the second object.

13. The medical imaging apparatus of claim 12, wherein the gantry suspends the first detector and the second detector from above the object.

14. The medical imaging apparatus of claim 12, wherein the gantry suspends the first detector from a first support arm and the gantry suspends the second detector from a second support arm.

15. The medical imaging apparatus of claim 12, wherein the electronic controller and data acquisition means comprises graphical user interface.

16. The medical imaging apparatus of claim 12, wherein the electronic controller and data acquisition means comprise graphical user interface capable of in at least one of a full-screen mode displaying information regarding one of the first object and the second object and a split-screen mode simultaneously displaying information regarding the first object and the second object.

17. A method of using a medical imaging system to acquire image data of one or more separate objects, the method comprising the steps of:
determining whether image data is to be acquired in a single-planar mode or a multi-planar mode;
upon determining that image data is to be acquired in a single-planar mode, acquiring simultaneously from one or more detectors image data of a first patient; and
upon determining that image data is to be acquired in a multi-planar mode, acquiring simultaneously from each of a plurality of detectors image data of a one of plurality of separate, discrete objects.

18. A method of using a medical imaging system to acquire image data of one or more patients, the method comprising the steps of:
determining whether image data is to be acquired in a single-planar mode or a multi-planar mode;
upon determining that image data is to be acquired in a single-planar mode, performing the substeps of:
positioning one or more detectors about a first patient for which the image data is to be acquired; and acquiring from the one or more detectors image data of the first patient; and upon determining that image data is to be acquired in a multi-planar mode, performing the substeps of:

positioning a plurality of detectors about a plurality of patients for which image data is to be acquired; and acquiring simultaneously from the plurality of detectors image data of the plurality of patients.

19. A computer program product for acquiring image data of one or more patients, the computer program product having a medium with a computer program embodied thereon, the computer program comprising:

computer program code for determining whether image data is to be acquired in a single-planar mode or a multi-planar mode;

computer program code for, upon determining that image data is to be acquired in a single-planar mode, acquiring from the one or more detectors image data of a first patient; and computer program code for, upon determining that image data is to be acquired in a multi-planar mode, acquiring simultaneously from a plurality of detectors image data of a plurality of patients.

20. A computer program product for simultaneously acquiring image data of one or more separated and displaced objects, the computer program product having a medium with a computer program embodied thereon, the computer program comprising:

computer program code for determining whether image data is to be acquired in a single-planar mode or a multi-planar mode;

computer program code for, upon determining that image data is to be acquired in a single-planar mode, configuring one or more of a plurality of detectors to acquire image data of a first one of the objects and acquiring from the one or more detectors image data of the first object; and computer program code for, upon determining that image data is to be acquired in a multi-planar mode, configuring a plurality of detectors to each acquire image data of a different one of the objects and acquiring simultaneously from each of the plurality of detectors image data of one of the objects.

* * * * *

UNITED STATES PATENT AND TRADEMARK OFFICE
CERTIFICATE OF CORRECTION

PATENT NO. : 6,774,371 B2
DATED : August 10, 2004
INVENTOR(S) : Garrard et al.

It is certified that error appears in the above-identified patent and that said Letters Patent is hereby corrected as shown below:

<u>Title page,</u>
Item [76], Inventors, insert:
-- Jody Garrard Elk Grove, California
  Jeffrey Hallet Livermore, California
  Moataz Karmalawy San Ramon, California --.

Signed and Sealed this

Twenty-fifth Day of April, 2006

JON W. DUDAS
*Director of the United States Patent and Trademark Office*